(12) United States Patent
MacArthur

(10) Patent No.: US 8,882,505 B2
(45) Date of Patent: Nov. 11, 2014

(54) PLACEMENT TOOL

(76) Inventor: Jonathan MacArthur, London (CA)

( * ) Notice: Subject to any disclaimer, the term of this patent is extended or adjusted under 35 U.S.C. 154(b) by 747 days.

(21) Appl. No.: 12/307,350

(22) PCT Filed: Jun. 27, 2007

(86) PCT No.: PCT/CA2007/001144
§ 371 (c)(1),
(2), (4) Date: Jul. 20, 2009

(87) PCT Pub. No.: WO2008/003162
PCT Pub. Date: Jan. 10, 2008

(65) Prior Publication Data
US 2010/0015569 A1    Jan. 21, 2010

Related U.S. Application Data

(60) Provisional application No. 60/817,689, filed on Jul. 3, 2006.

(51) Int. Cl.
*A61C 3/00*    (2006.01)
*A61C 5/06*    (2006.01)
*A61C 3/08*    (2006.01)

(52) U.S. Cl.
CPC ... *A61C 3/08* (2013.01); *A61C 5/06* (2013.01); *A61C 3/00* (2013.01); *A61C 3/005* (2013.01)
USPC .......................................................... 433/141

(58) Field of Classification Search
CPC .............. A61C 3/00; A61C 3/08; A61C 5/06; A61C 5/04; A61C 3/005; B32B 37/12
USPC ............. 433/2–24, 27, 29, 31–32, 50, 52, 75, 433/114, 141, 146–147, 152–154, 156–158, 433/161–163; 362/573; 156/349, 499, 578; D08/30, 14.1, 29.1, 29.2; 206/223, 206/541, 571, 572, 575, 574
See application file for complete search history.

(56) References Cited

U.S. PATENT DOCUMENTS

| | | | | |
|---|---|---|---|---|
| 4,082,940 A * | 4/1978 | Knowles et al. | .............. | 219/239 |
| 4,457,457 A | 7/1984 | Dziki | | |
| 5,256,064 A * | 10/1993 | Riihimaki et al. | ............ | 433/141 |
| 5,320,533 A * | 6/1994 | Lee | ............................... | 433/218 |
| 5,664,701 A * | 9/1997 | Massena | .................... | 222/146.5 |
| 6,083,558 A * | 7/2000 | Bremont | ....................... | 427/195 |
| 6,634,051 B1 * | 10/2003 | Dragan et al. | .................. | 15/106 |
| 7,303,392 B1 * | 12/2007 | Schermerhorn et al. | ........ | 433/36 |
| 2004/0237233 A1 * | 12/2004 | Dragan et al. | ............. | 15/104.94 |

* cited by examiner

*Primary Examiner* — Cris L Rodriguez
*Assistant Examiner* — Mirayda A Aponte
(74) *Attorney, Agent, or Firm* — Katten Muchin Rosenman LLP

(57) ABSTRACT

A method and a kit for the positioning of a small object, such as a dental restoration, in a specific desired location, includes a handle portion and a head portion having bristles. The method includes the steps of placing a non-molten glue pellet on the exterior surface of the object, applying heat to the pellet to melt it, positioning a head portion of a restoration placement device having bristles in the melted glue to receive the object on the end portion of the device, placing the object in its desired location, and removing the restoration placement device from the object.

2 Claims, 11 Drawing Sheets

PLACEMENT TOOL

This application is a national stage of PCT/CA2007/001144, filed on Jun. 27, 2007, which claims priority to U.S. Provisional Application No. 60/817,689, filed on Jul. 3, 2006, the entire contents and disclosure of which are hereby incorporated by reference.

FIELD OF THE INVENTION

The present invention relates to a method for accurate positioning of a small object to be secured at a specific place. The present invention also provides a device and kit for positioning such an object. The present invention further provides a method for positioning a dental restoration on a tooth, and more particularly relates to the use of a placement device for the positioning of a dental restoration on a tooth.

BACKGROUND OF THE INVENTION

There are many situations in life that require the accurate placement of small objects. Generally the accurate placement of a small object is hindered by a user's hands and an inability to control their grip and/or release on an object at a specific position. Examples of such situations include modelling and craft applications, i.e scrap booking and jewellery making.

One situation that requires the accurate placement of a small object occurs in the dental field. Conventional techniques to secure inlays, onlays, crowns and veneers (dental restorations) have depended upon various rod-like handles tipped with sticky wax or nectar-like bulbs. These techniques are generally limited in their effectiveness due to their weak and unpredictable bond. Since the restoration once "held" by such handles is subject to multiple manipulations prior to final placement the tenuous bond provided by present alternatives is often stressed to the point of failure. The placement of these small dental restorations is the culmination of much effort and it is crucial that the grip described is reliable but also easily removable once final placement is achieved.

Different options have been discussed in the dental community to overcome some of the problems of the known methods discussed above. It is generally acknowledged that existing products are inadequate. One suggestion advanced has been to use a light cured bonding agent normally used to bond standard dental composite restorations. The technique suggested has been to bond a brush unto the restorative surface. This technique provides a more stable bond than other presently marketed techniques but is time consuming, requires two people to perform, and is not cost effective. The brush is also often difficult to remove after placement and residual bond left behind on the restoration is clear and hence difficult to see. Its complete removal after requires the use of a dental drill, which can mar the previously polished or glazed finish.

Thus, there is a need for an improved method and for a device useful for object positioning.

SUMMARY OF THE INVENTION

Such a device and method have now been developed.

Thus, in one aspect, the present invention provides a method of positioning a dental restoration, having an interior surface and an exterior surface, on a tooth, comprising the steps of (i) placing on the exterior surface of the dental restoration at least one glue pellet, (ii) applying heat to the at least one glue pellet to melt the glue pellet; (iii) positioning an end portion of a restoration placement device into the melted glue pellet and thereby receiving the glue pellet thereon; (iv) applying a tooth bonding material to the interior surface of the dental restoration; (v) positioning the dental restoration on the tooth; and (vi) removing the restoration placement device from the restoration.

In one embodiment, the step of applying a heat source to the at least one glue pellet uses a portable heat source. In a further embodiment, the at least one glue pellet is dispensed from a spring-loaded glue pellet cassette, or from a cassette comprising multiple pellet-containing compartments. In an alternative embodiment, the restoration placement device comprises a plurality of bristles extending outwardly from the end portion.

In an additional aspect, the present invention provides a method of mounting a dental restoration onto a restoration placement device comprising the steps of (i) placing on the exterior surface of the dental restoration at least one glue pellet; (ii) applying heat to the at least one glue pellet to melt the glue pellet; and (iii) positioning an end portion of the restoration placement device into the melted glue pellet.

In a further aspect, the present invention provides a dental restoration placement device comprising a handle portion and a substantially flat head portion connected to one end of the handle portion, said head portion comprising a plurality of bristles extending therefrom, the head portion being operable to bend relative to the handle portion and having sufficient bristles operable to extend into and secure onto molten glue. The present invention also provides for the use of the dental restoration brush described herein.

In a further aspect, the present invention provides a dental restoration kit comprising a placement device having a head portion comprising a plurality of bristles extending therefrom and at least one glue pellet sized to receive the head portion of the placement device when in a molten state.

In an alternative embodiment, the present invention provides a dental restoration kit comprising a placement device having a head portion comprising a plurality of bristles extending therefrom, a glue pellet cassette, comprising a plurality of glue pellets, operable to dispense individual glue pellets and a portable heat source operable to melt a glue pellet.

In an alternative embodiment, the present invention provides a placement device comprising a handle portion and a head portion, connected to one end of the handle portion, the head portion being operable to bend relative to the handle portion and being of sufficient size to extend into and secure onto molten glue. The present invention also provides for the use of the dental restoration device described herein. In one embodiment, the head portion comprises a plurality of bristles extending therefrom which are operable to extend into and secure a molten glue pellet.

In a further aspect, the present invention provides an adhesion kit comprising a placement device having a flexible handle portion and a head portion and at least one glue pellet sized to receive the head portion of the placement device when the glue pellet is in a molten state. The placement device may also include a plurality of bristles extending from the head portion thereof.

In an alternative embodiment, the present invention provides an adhesion kit comprising a placement device having a head portion comprising a plurality of bristles extending therefrom, a glue pellet cassette, comprising a plurality of glue pellets, operable to dispense individual glue pellets and a portable heat source operable to be received by at least one glue pellet and to apply heat thereto. The glue pellet cassette is operable to releasably attach to the heat source.

BRIEF DESCRIPTION OF THE DRAWINGS

The invention will be described below in further detail with particular reference to the accompanying drawings in which.

DETAILED DESCRIPTION OF THE PREFERRED EMBODIMENTS

The present invention provides a device and kit, and a method of using the device and/or kit, for positioning and maintaining objects in a required place and, in particular, objects that are to be adhered to a surface. For example, the method and device and/or kit may be used to position an object in a craft project to a surface, such as a jewel to a costume. Alternatively the device and/or kit may be used by a dentist to position a dental restoration on a tooth. The present method and device are particularly useful to position an object in a location that is generally difficult to otherwise access.

The present invention provides a user with a tool that allows for easy and precise placement of an object at a desired position. In particular, the invention allows a user to place a small object at a precise location while only requiring the use of one hand.

The present invention will be described in further detail in relation to the dental application. However, it will be understood that this embodiment is not meant to be limiting for the use of the device and/or kit.

Thus, in one embodiment, the present invention provides a method for positioning a dental restoration on a tooth. It will be understood by a person skilled in the art that a dental restoration may include inlays, onlays, crowns, veneers and the like.

Figure 4:
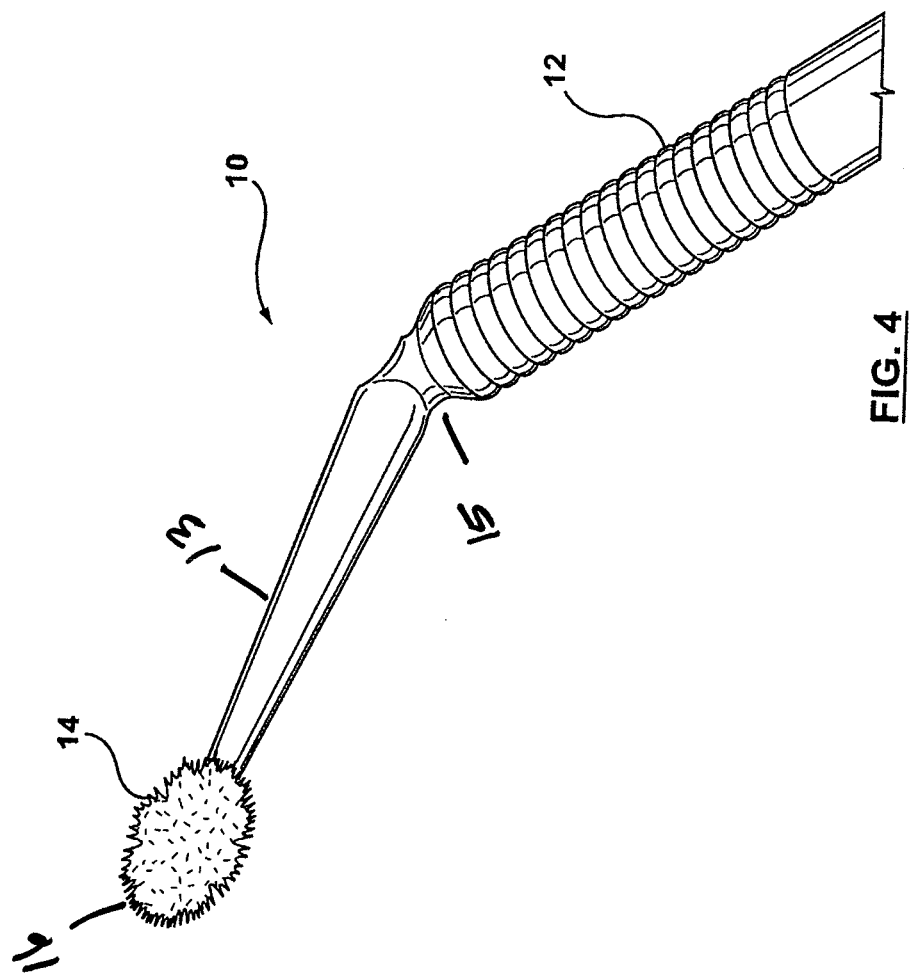
FIG. 4 is a photograph of one embodiment of a dental placement device that may be used in the present invention.

The present invention includes the use of a dental placement device, or microbrush, that is illustrated in FIG. 4 at numeral 10. The dental placement device of the present invention includes a handle portion 12 and a head portion 14. A stem 13 fastens the head portion 14 to the handle portion 12 at connection point 15. As can be clearly seen in FIG. 4, the head portion 14 is flexibly attached to the handle portion 12 and is operable to rotate, bend and/or flex about the connection point 15 to assist the user with the correct positioning of a dental restoration as well as to assist in the removal of the device and glue from the restoration, described below in further detail, following placement of the restoration.

In one embodiment, shown in FIG. 4, the head portion 14 includes a plurality of bristles 16 extending therefrom. The bristles 16 are sized and positioned in order to be operable to spread out into molten glue when in use. The ability of the bristles 16 to extend outwardly provides secure attachment to the molten glue when in use, allowing the user to remove the glue with the brush when required, described in further detail below.

Figure 5:
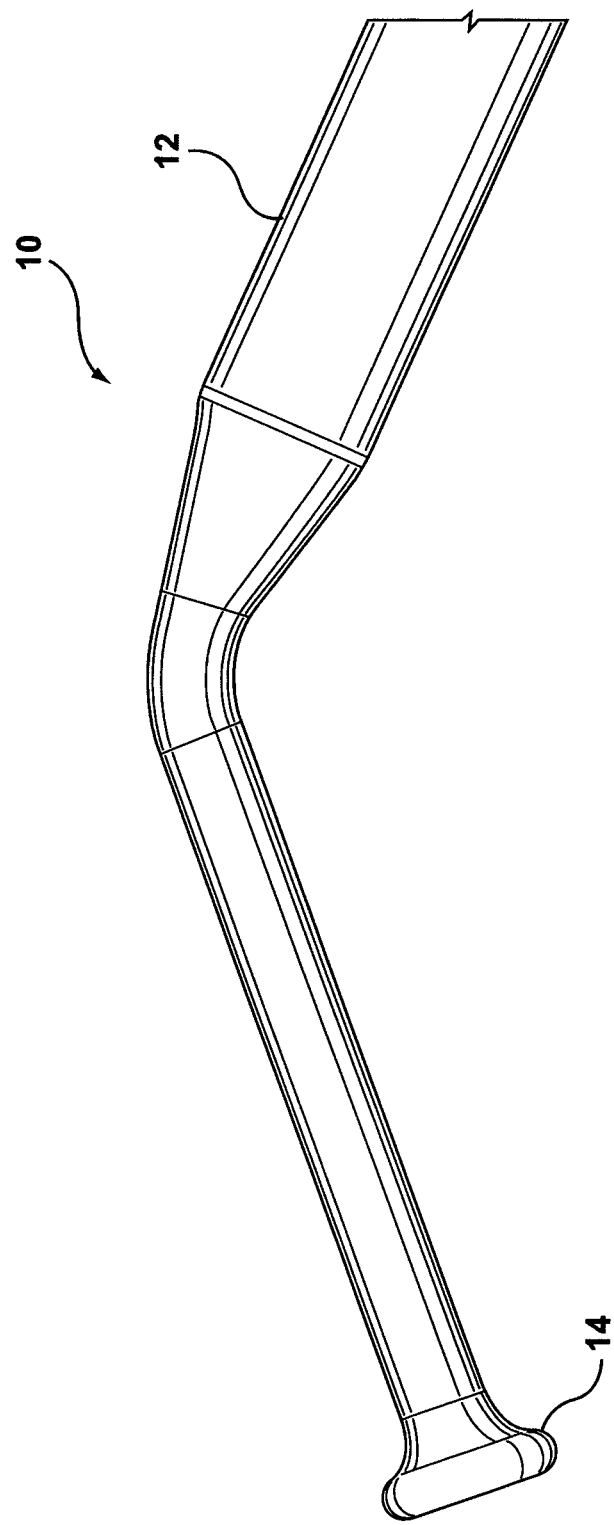
FIG. 5 is a photograph of an alternative embodiment of a dental placement device that may be used in the present invention.
Figure 8:
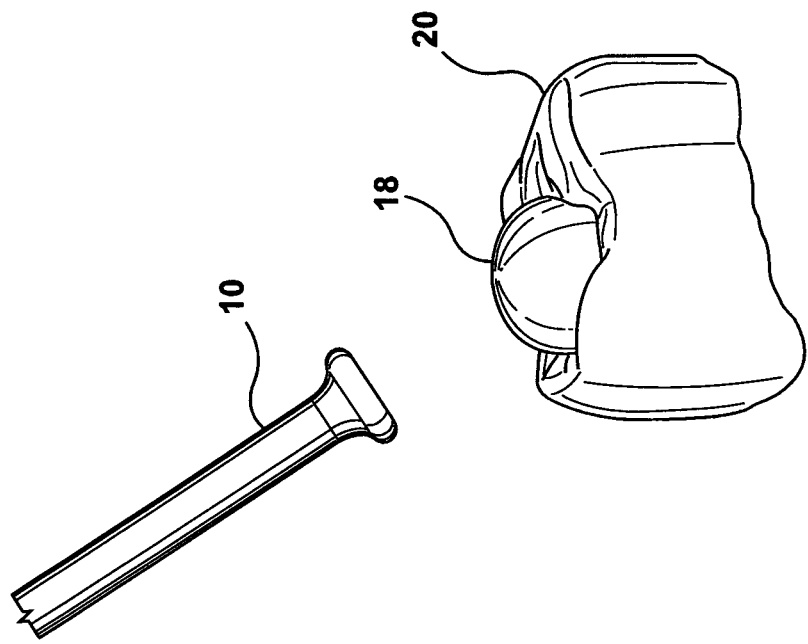
FIG. 8 is a photograph of a dental placement device being positioned adjacent the dental restoration illustrated in FIG. 7.
Figure 9:
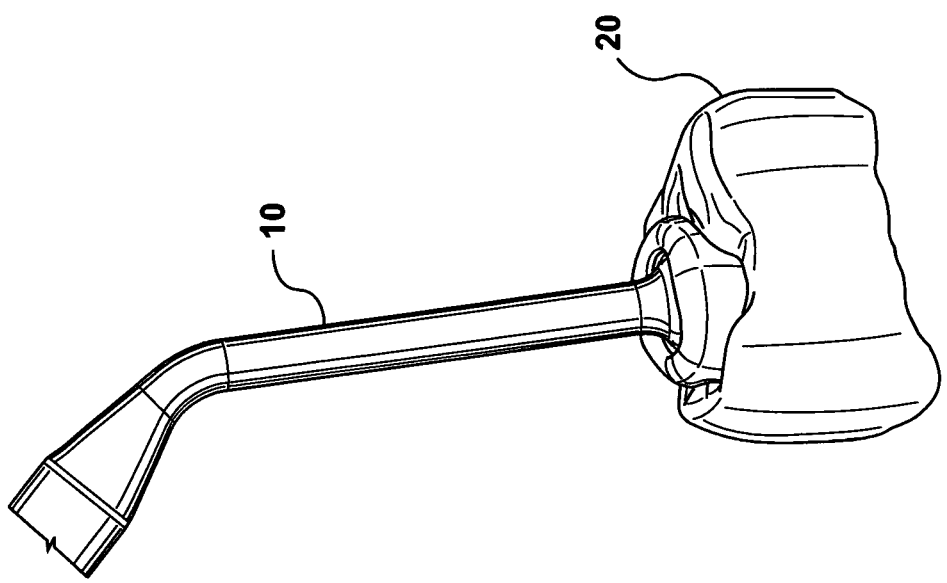
FIG. 9 shows a dental placement device positioned in the molten glue on the dental restoration illustrated in FIG. 7.

In an alternative embodiment, shown in FIG. 5, the head portion 14 is substantially flat and does not include bristles, however the profile of the head portion 14 is sufficient to provide an effective surface for attachment of the head portion to the molten glue, as seen in FIGS. 8 and 9. As will be appreciated by one of skill in the art, the head portion 14 may be otherwise shaped, including for example, round or oval.

As one of skill in the art will appreciate, the placement device is made of materials conventionally used for similar such devices, for example, metals, hard plastics, rubber, etc., which are appropriate to permit the device to function. For a dental placement device, the materials will, of course, be suitable for use of the device in the mouth of a patient. In addition, the components of the device, such as the head portion and the handle portion, may be made of the same materials or different materials. In this regard, the handle and head portions of the device may be unitary in construction, or may be distinct components that fit together to form the device.

Figure 7:
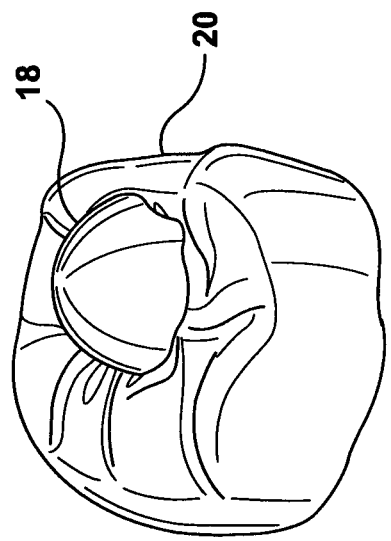
FIG. 7 is a photograph of a dental restoration including a molten glue pellet thereon.
Figure 10:
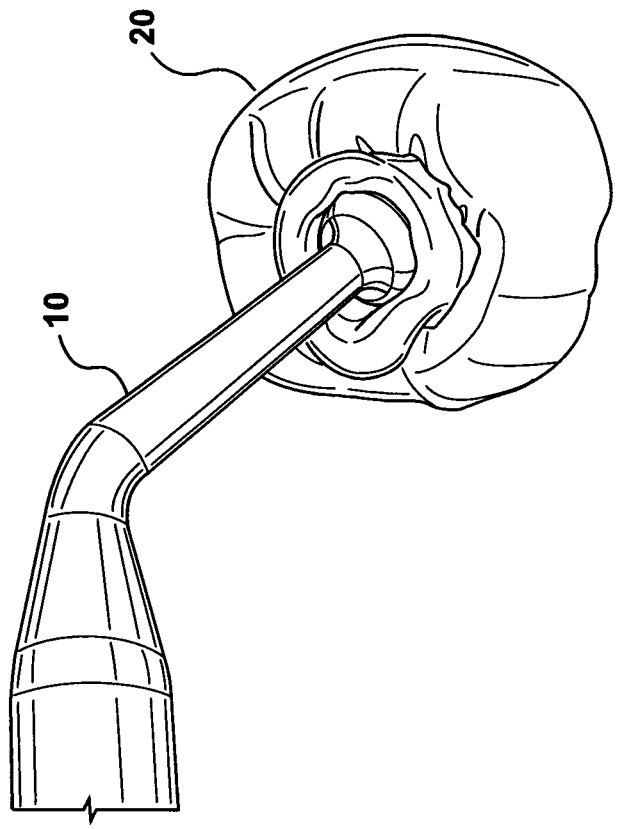
FIG. 10 shows a dental placement device positioned in the molten glue on the dental restoration illustrated in FIG. 7.

The method for positioning a dental restoration on a tooth includes the initial step of placing at least one glue pellet 18 on the exterior surface of the dental restoration 20. It will be understood that the term "exterior surface" means the surface that will face outwardly when the dental restoration is placed on the tooth. In a preferred embodiment, only one glue pellet 18 is required and the pellet is sized such that when it is in the molten state it is received on the surface of the restoration 20 and, as can be seen in FIG. 7, covers a portion of the surface of the restoration sufficient to provide a secure connection to the placement device 10 to allow for easy control and placement by the user. In one embodiment, pellets of varying sizes are provided for use with dental restorations of different size. In this embodiment, the pellets may be of different colours, including being clear, each colour representing a different size to allow a user to easily choose the preferred size.

Figure 1:
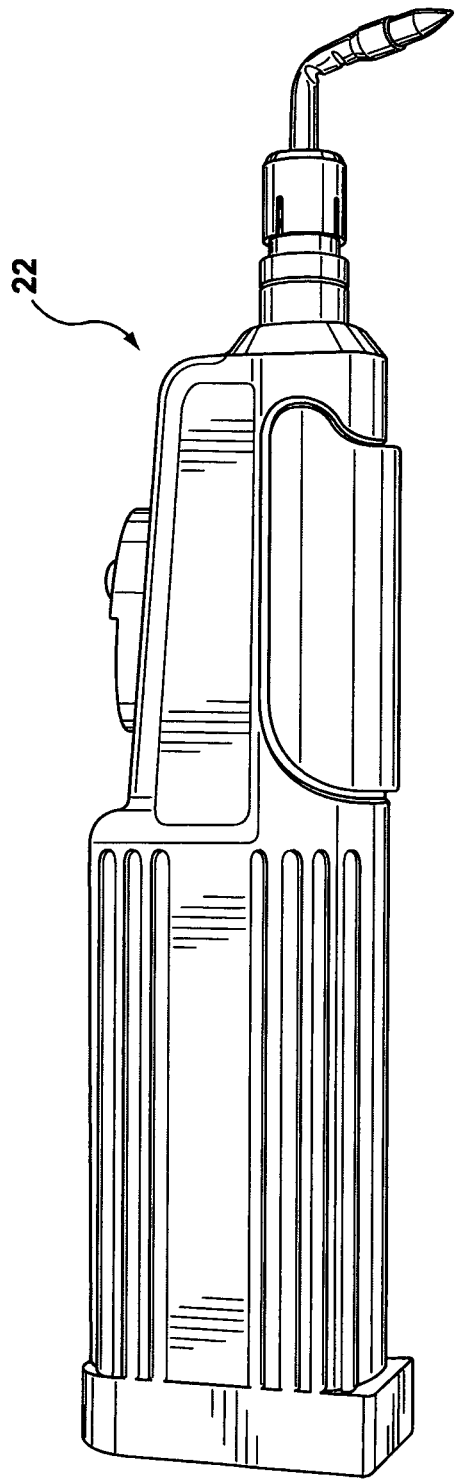
FIG. 1 shows a side perspective view of a portable heat source that may be used in the present invention.
Figure 2:
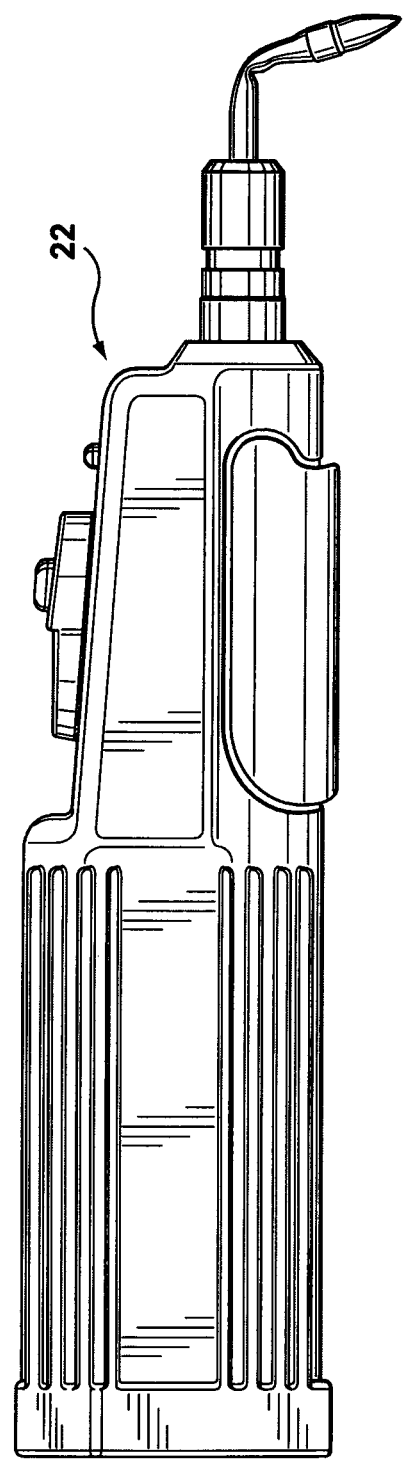
FIG. 2 shows a side view of a portable heat source that may be used in the present invention.
Figure 3:
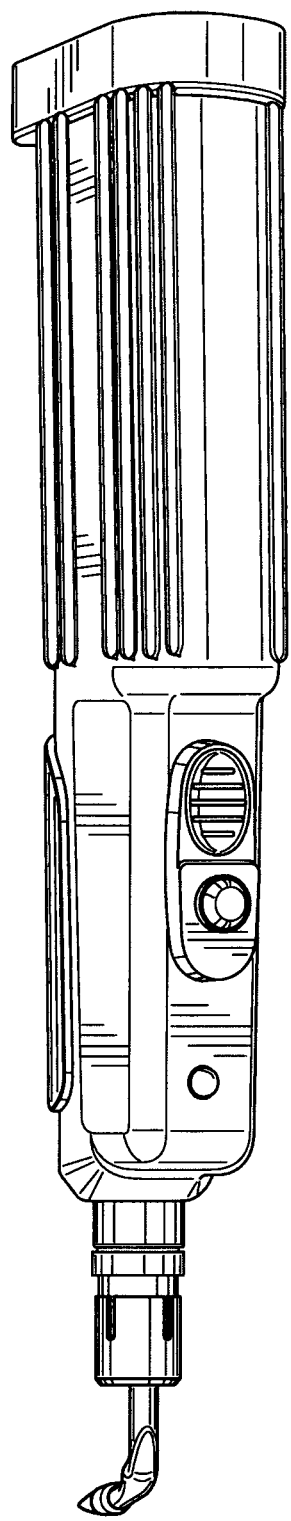
FIG. 3 shows a front perspective view of a portable heat source that may be used in the present invention.

In a preferred embodiment the pellets 18 are disc shaped and include a perforation in the centre. The perforated centre allows for the placement of a heating device 22, shown in FIGS. 1-3, within the centre to pick up the disc and move to the required position. Preferably the discs are 1-2 mm thick and have a diameter of 3-4 mm.

Figure 13:
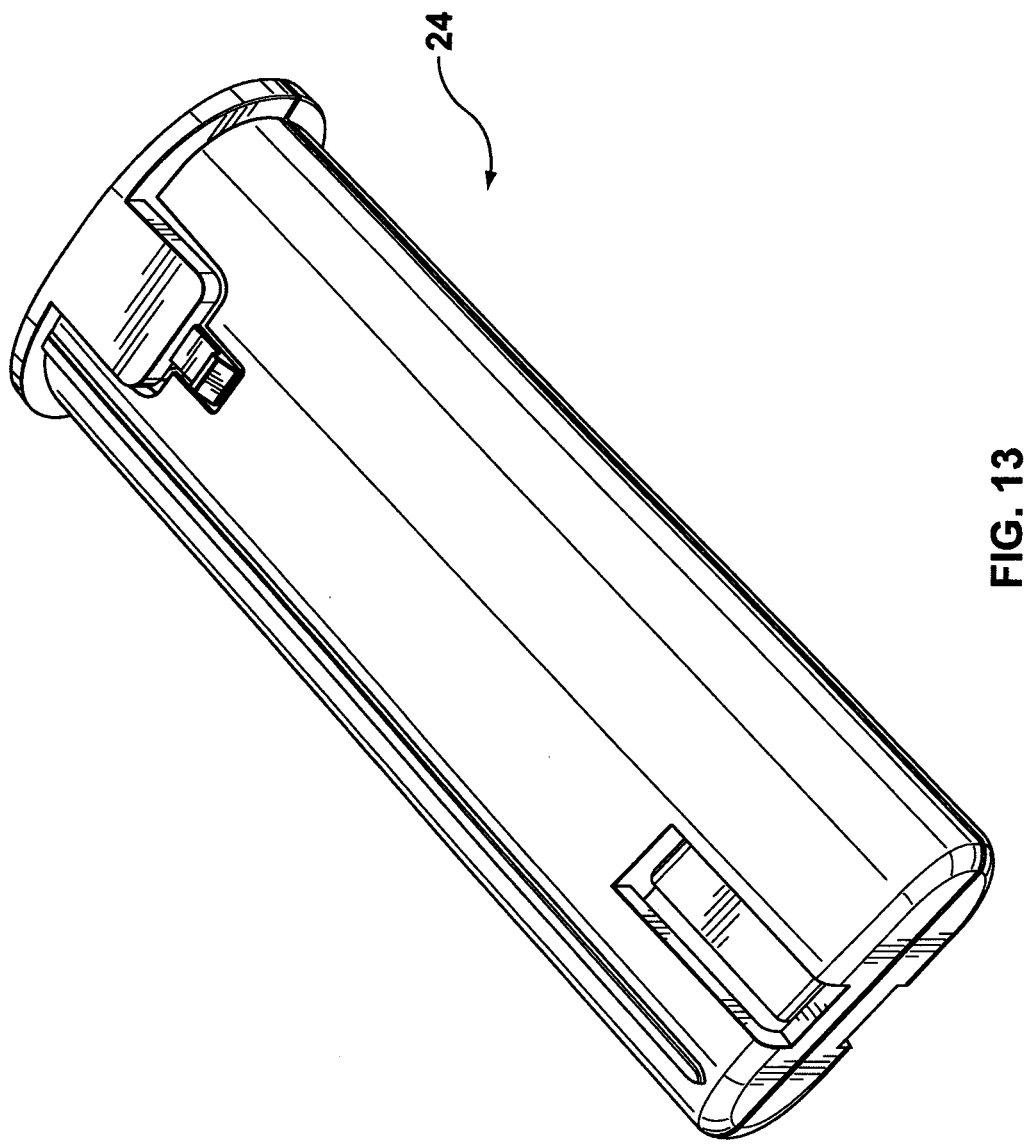
FIG. 13 shows a side perspective view of a glue pellet cassette according to the present invention.
Figure 14:
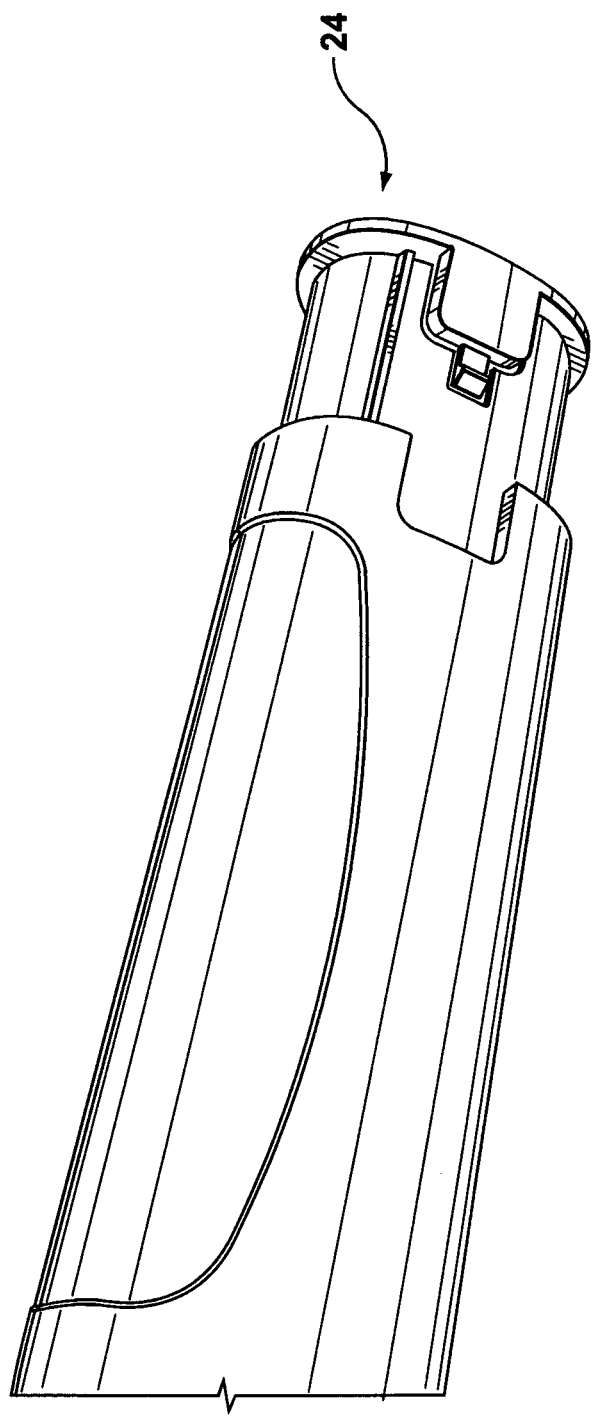
FIG. 14 shows another side perspective view of a glue pellet cassette, according to the present invention.

In a further embodiment, a glue pellet cassette 24, shown in FIGS. 13 and 14, is provided for easy dispensing of the glue pellets. The cassette is spring-loaded and allows a user to remove one pellet at a time through an aperture that is opened by a dispensing mechanism in a manner known in the art. Alternative dispensing cassettes may also be used, as will be appreciated by one of skill in the art. In another example, a cassette comprising multiple pellet-containing compartments may be used including a rotatable dispensing mechanism, or a rotatable cover with a window opening allowing a single compartment only to be open to release the desired glue pellets. The glue pellet cassette 24 may also be operable to connect to a portion of the surface of the portable heating device 22. For example, the cassette 24 may include a groove or clip that allows attachment to the portable heating device 22 handle for convenient storage and transport.

Figure 6:
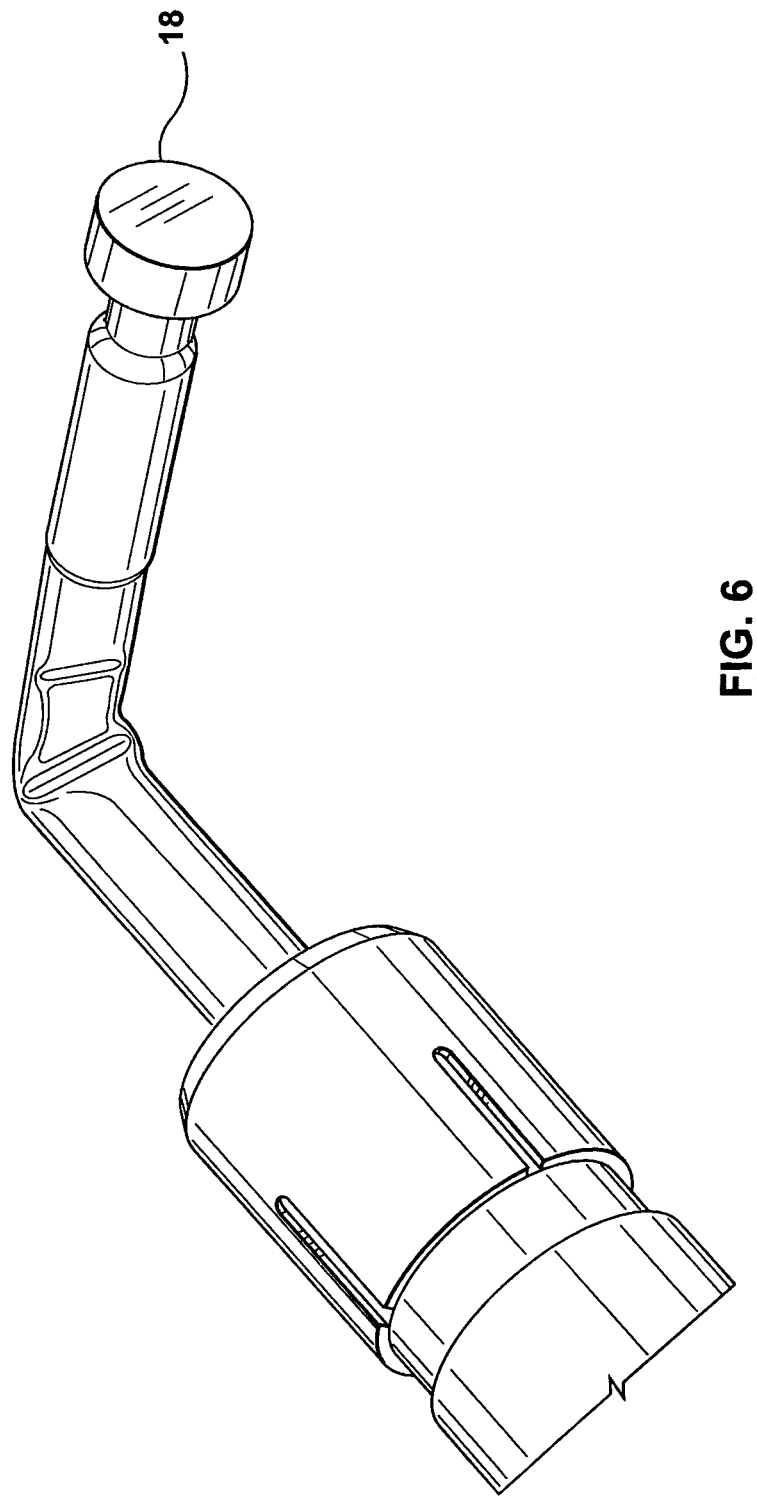
FIG. 6 is a photograph of a portable heat source attached to a glue pellet.

Once the glue pellet 18 has been positioned on the dental restoration, a heating device 22, for example a portable heating device 22 as seen in FIG. 6, is used to apply heat to the glue pellet 18 and melt the glue pellet 18. In one embodiment, the heating device 22 is a portable heating device, such as a soldering unit or a laser or electro surgical unit. Preferably the portable heating device 22 is a portable battery operated soldering unit. The heating device 22 will be activated for a time sufficient to turn the glue pellet 18 into a liquid globule. It will be understood that a person skilled in the art will know the time required to apply heat using the heating device or source to achieve the desired molten state of the glue. A suggested time for applying the heat using the heat source is approximately 5 seconds. Heating time can be varied to alter the degree of adhesion.

Figure 12:
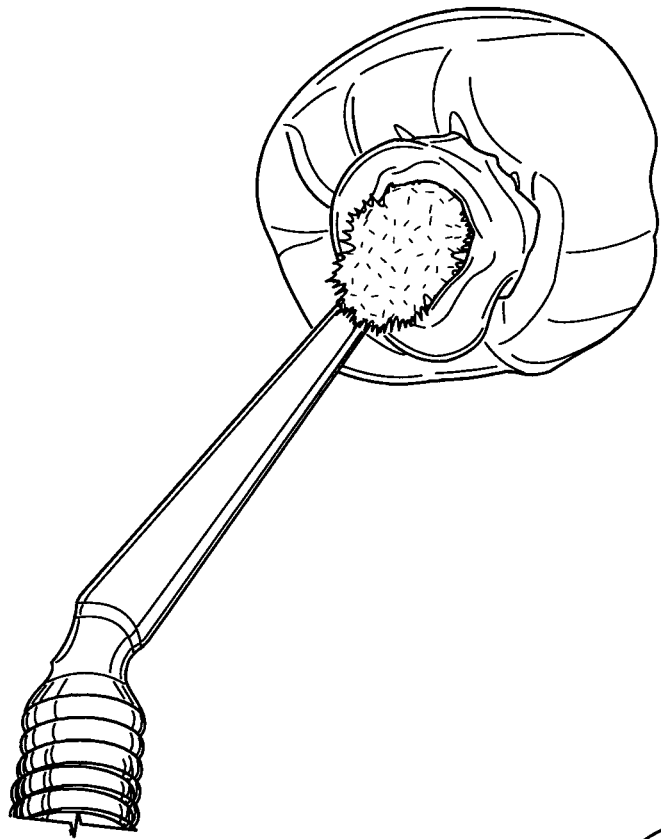
FIG. 12 illustrates the connection of an alternative embodiment of a dental placement device with a glue pellet according to the present invention.

Once the heat has been applied and the glue is in a sufficient molten or liquid state, the heating device 22 is removed from the glue, see FIG. 7. While the glue is still in a molten state the head portion 14 of the placement device 10 is placed, or plunged, into the liquid glue, as illustrated in FIGS. 8 and 9. The head portion 14 is positioned to be received in the glue at a position that allows a user to have sufficient control in handling and positioning the restoration, i.e. preferably the head portion is centrally received within the glue. In the embodiment in which the head portion 14 includes bristles 16, when the head portion 14 is placed into the glue the bristles 16 extend outwardly therefrom into the liquid glue, as seen in FIG. 12. The position and size of the bristles 16 allow them to spread out into the glue and provide a secure connection between the placement device 10 and the glue. In the alternative embodiment in which the placement device includes a substantially flat head with no bristles, the head portion is received in the molten glue at a position that allows for sufficient connection between the flat head portion and the glue to provide a secure attachment therebetween, as illustrated in FIG. 9.

Prior to placement of the restoration on a tooth, a tooth bonding material is applied to the interior surface of the restoration, i.e. the surface of the restoration which comes in contact with the tooth and is seated on the tooth. The tooth bonding material is of the type conventionally used.

Figure 11:
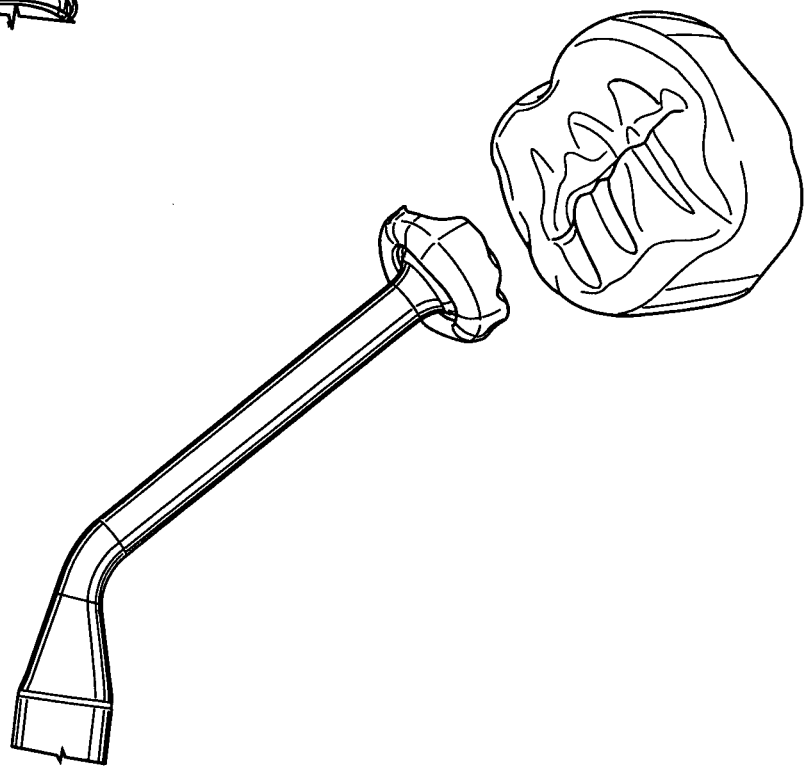
FIG. 11 illustrates the removal of a glue pellet form a dental restoration using a dental placement device according to the present invention.

The restoration may then be placed on the tooth where desired. It will be understood that the connection of the restoration to the tooth will be by means known in the art. Once the restoration has been placed on the tooth, the flexible handle of the placement device 10 may be bent, as required, to facilitate final placement of the restoration. Once the final placement has been achieved, the device 10 can be pulled away from the restoration, separating the head portion, including the glue attached thereto, from the restoration as seen in FIG. 11.

It will be understood that the glue is readily removed or lifted from the restoration with the placement device due to the secure placement of the head portion within the glue. This secure placement is advantageously enhanced with bristles in the head portion. Any glue remaining on the dental restoration is easily identified by its colour and can readily be removed by peeling the glue from the restoration.

The use of the invention will clearly be understood by the above embodiment and can be adapted to other situations that require the placement of an object at a specific location, and in particular at a location that requires controlled and accurate placement by a user. For example, in costume jewellery there are generally numerous small jewels and the like the positioning of which require high precision with low tolerance. Many craft and modelling activities require similar levels of glue placement precision. Eliminating the need for proximity to a wall electrical outlet is also an attractive feature provided by a cordless heating element. Such work can be tremendously fiddly requiring accurate control by a designer in placing the jewels at specific locations. The invention provides a tool that can assist. A glue pellet, or portion thereof, may be placed on the jewel to be positioned and then heat can be applied to transform the glue to its molten state. The head of the placement tool may then be placed in the molten glue to adhere the device to the jewel. Once the tool is placed in the molten glue, additional glue may be positioned on the opposite surface of the jewel, or alternatively glue may be placed at the location at which the jewel is to be placed. The user may then position the jewel at the appropriate location using the flexible handle portion to accurately position the jewel. Once in place and adhered on the surface the user can remove the tool with the glue portion from the jewel and continue with the work. It will be understood that this embodiment employs a similar use to that described above.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments. Further, all of the claims are hereby incorporated by reference into the description of the preferred embodiments.

The invention claimed is:

1. A method of positioning a dental restoration, having an interior surface and an exterior surface, on a tooth, comprising the steps of:
   (i) placing on the exterior surface of the dental restoration at least one non-molten glue pellet;
   (ii) applying heat to the at least one non-molten glue pellet on the dental restoration to melt the at least one glue pellet;
   (iii) positioning a head portion of a dental placement device into the melted glue pellet and allowing the head portion to become securely adhered thereto, wherein the head portion comprises a plurality of bristles extending outwardly therefrom;
   (iv) applying a tooth bonding material to the interior surface of the dental restoration;
   (v) positioning the dental restoration on the tooth using the placement device; and
   (vi) removing the restoration placement device with attached non-molten glue pellet from the dental restoration.

2. The method of claim 1, wherein heat is applied to the glue pellet with a portable heat source.

* * * * *